(12) United States Patent
Robertson

(10) Patent No.: US 8,006,846 B2
(45) Date of Patent: Aug. 30, 2011

(54) PORTABLE MEDICINE CASE

(76) Inventor: Sondra T. Robertson, Wilmington, NC (US)

( * ) Notice: Subject to any disclaimer, the term of this patent is extended or adjusted under 35 U.S.C. 154(b) by 0 days.

(21) Appl. No.: 12/804,411

(22) Filed: Jul. 21, 2010

(65) Prior Publication Data

US 2011/0017624 A1 Jan. 27, 2011

Related U.S. Application Data

(60) Provisional application No. 61/271,510, filed on Jul. 22, 2009.

(51) Int. Cl.
*B65D 69/00* (2006.01)
(52) U.S. Cl. .................. 206/570; 206/438; 206/479
(58) Field of Classification Search .............. 206/231, 206/363, 370, 438, 472, 473, 477, 478, 479, 206/570–572
See application file for complete search history.

(56) References Cited

U.S. PATENT DOCUMENTS

| | | | | |
|---|---|---|---|---|
| 1,508,204 A | * | 9/1924 | Walker | 206/479 |
| 1,991,306 A | * | 2/1935 | Woolsey | 206/479 |
| 4,429,793 A | * | 2/1984 | Ehmann | 206/570 |
| 4,523,702 A | * | 6/1985 | Viio | 206/479 |
| 6,109,442 A | * | 8/2000 | Roegner | 206/479 |
| 6,779,665 B2 | * | 8/2004 | Bolanos | 206/570 |
| 6,935,133 B2 | * | 8/2005 | Keeter et al. | 206/570 |
| 7,565,979 B1 | * | 7/2009 | Gibson | 206/570 |
| 2008/0141700 A1 | * | 6/2008 | Fuchs | 206/570 |

* cited by examiner

*Primary Examiner* — Luan K Bui
(74) *Attorney, Agent, or Firm* — MacCord Mason PLLC

(57) ABSTRACT

A portable carrying case is described to hold medicine vials during travel, doctors' visits, etc. The case includes an open-topped box with a hinged lid and attachment means to secure the lid to the box. The case further includes a vial support platform, which may be the upper surface of the box, or a separate platform attachable to the box bottom wall. The platform has a plurality of spaced, parallel divider walls having lower edges attached to the support surface and upper edges. The divider walls have aligned left holes and aligned right holes. An elastic cord is slidable through aligned holes to cord ends outside an end divider wall. A cord lock is used to adjust the length of the cord. The support surface, walls and cord form a plurality of adjustable vial receiving compartments, with the force on each vial being equal regardless of differences in vial sizes.

20 Claims, 2 Drawing Sheets

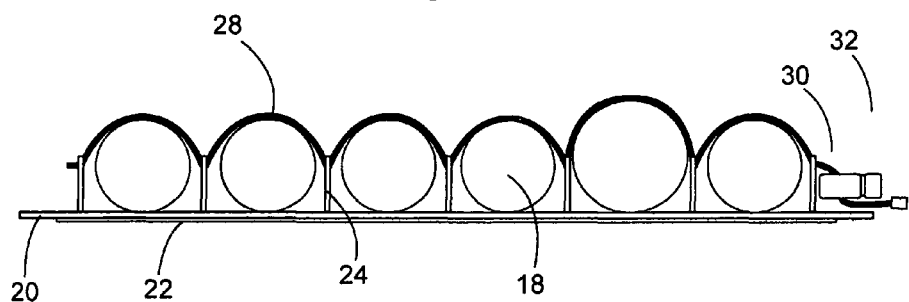
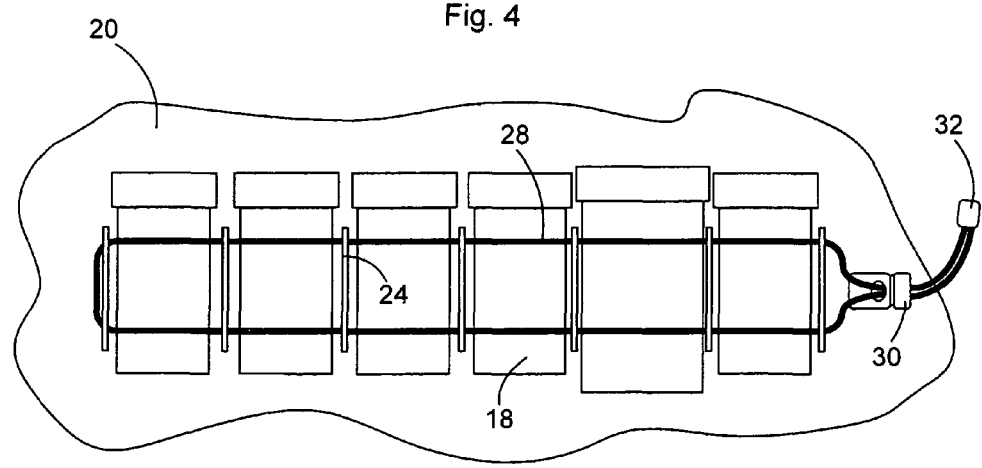

PORTABLE MEDICINE CASE

This application claims the benefit of the filing date of, and incorporates by reference, U.S. Provisional Application Ser. No. 61/271,510, Filed Jul. 22, 2009, entitled Portable Medicine Case.

BACKGROUND OF THE INVENTION (1) Field of the Invention

The present invention relates generally to a portable case for organizing and transporting medicine vials, and in particular to a portable medicine case designed to securely hold medicine vials of different sizes.

(2) Description of the Prior Art

When traveling, an individual must carry with them all of the medication required while away from home. In addition, physicians request that patients bring with them all of their prescription medication so that the physician can verify the details of each prescription to ensure that there is no conflict between multiple prescriptions. Often, individuals simply dump their prescription vials into a paper bag or other holder, which makes it difficult to ascertain if all prescriptions have been included, and difficult to locate a particular prescription.

Various carrying cases have been proposed in the prior art for addressing the need for an organized way to carry prescription vials, the term "vials" referring generally to all containers of prescription medicines. Generally, these prior art cases are comprised of a box with a hinged lid. The box may simply include a storage space for placement of the vials, or may include some means for securing a plurality of vials inside the storage space. However, in those instances where a means for securing the vials, e.g., elastic loops, is provided, no provision is made for securing vials of different diameters. Thus, relatively small vials may not be securely held and relatively larger vials may not fit into the securing means.

SUMMARY OF THE INVENTION

The present invention addresses this shortcoming in prior art medicine cases by providing an adjustable means for securing a plurality of medication vials within the storage space within a medication case. In accordance with the present invention, a plurality of vials can be held in side-by-side arrangement with equal force being exerted on each of the vials to secure the vials in position, even when the vials are of different diameters or when vials are not inserted into all of the vial compartments.

Overall, the present medicine case is comprised of an open-topped box having a bottom wall, spaced parallel side walls and spaced parallel end walls, the side and end walls extending upwardly from the outer periphery of the bottom wall to common upper edge. A lid is hinged to one of the side walls to extend over the box. Attachment means, e.g., a zipper, is provided to secure the lid about the upper wall of the box, thereby protecting and preventing accidental spillage of the box contents. The lid may include one or more pockets on its inner face for handy storage of prescription information, medical alert information, appointment cards, a calendar, pens, etc. The case may also include a carrying handle and/or a shoulder strap.

Uniquely, the medication case of the present invention also includes a vial support surface with a plurality of spaced divider walls having lower edges attached to the support surface and upper edges, preferably generally parallel to the lower edges. The divider walls may be spaced equidistant from each other, or at different spacing. Preferably, the walls are of a flexible material. The vial support surface may be the upper surface of the box bottom wall. Preferably, however, the vial support surface is the upper surface of a planar platform that is releasibly attached to the upper surface of the bottom wall, e.g., with hook and loop fastener, the mating segments of which are attached to the bottom surface of the platform and the upper surface of the bottom wall.

Each wall includes a pair of spaced left and right holes adjacent its top edge. Preferably, a grommet is inserted in each hole to minimize tearing. An elastic cord, e.g., a bungee cord, extends from outside one of the end walls through the aligned left holes, loops around the outer surface of the opposed end wall, and returns through the aligned right holes to the outside of the first end wall to form two parallel cord segments. The two cord ends are then inserted through a spring-loaded cord lock. The cord lock can be squeezed to slide the lock up and down the two cord segments, thereby adjusting the length of the looped cord. The ends of the cord can be tied together, or clamped together by a cord pull.

The vial support surface, divider walls and elastic cord together create a plurality of adjacent vial compartments, each compartment being comprised of the inner faces of the adjacent walls, the segment of the support surface extending between the adjacent walls, and the two cord segments that extend above the support surface and between the adjacent walls.

The storage space within the box may include a single row of spaced divider walls, thereby creating a single row of vial compartments. Preferably, however, the case includes at least two parallel rows of spaced divider walls to create at least two rows of vial compartments, thereby increasing the number of vials that can be stored. The number of vials that can be stored will depend on the case size and number of rows. However, a case with two rows, each capable of holding six vials will be adequate for most individual needs.

The case can be made of various materials and may be rigid or flexible. For example, the case can be made of a waterproof or water resistant fabric, such as ripstop nylon, which also provides wear resistance. The walls and lid may be padded to provide additional protection to the contents.

When used, the medicine vials are inserted into the compartments beneath the elastic cord segments. The cord segments are raised by each vial to a height dependent on the diameter of the vial. The cord is then tightened with the cord lock to tension the cord and press it against the vials. Insertion of vials into all compartments is not required. When tightened, the cord slides through the grommets, thereby equalizing the force exerted against the vials even when the vials are of different sizes.

BRIEF DESCRIPTION OF THE DRAWINGS

FIG. 3 is a sectional side view of one row of vials secured within the adjustable vial compartments.

FIG. 4 is a sectional top view of one row of vials secured within the adjustable vial compartments.

DETAILED DESCRIPTION OF THE INVENTION

Figure 1:
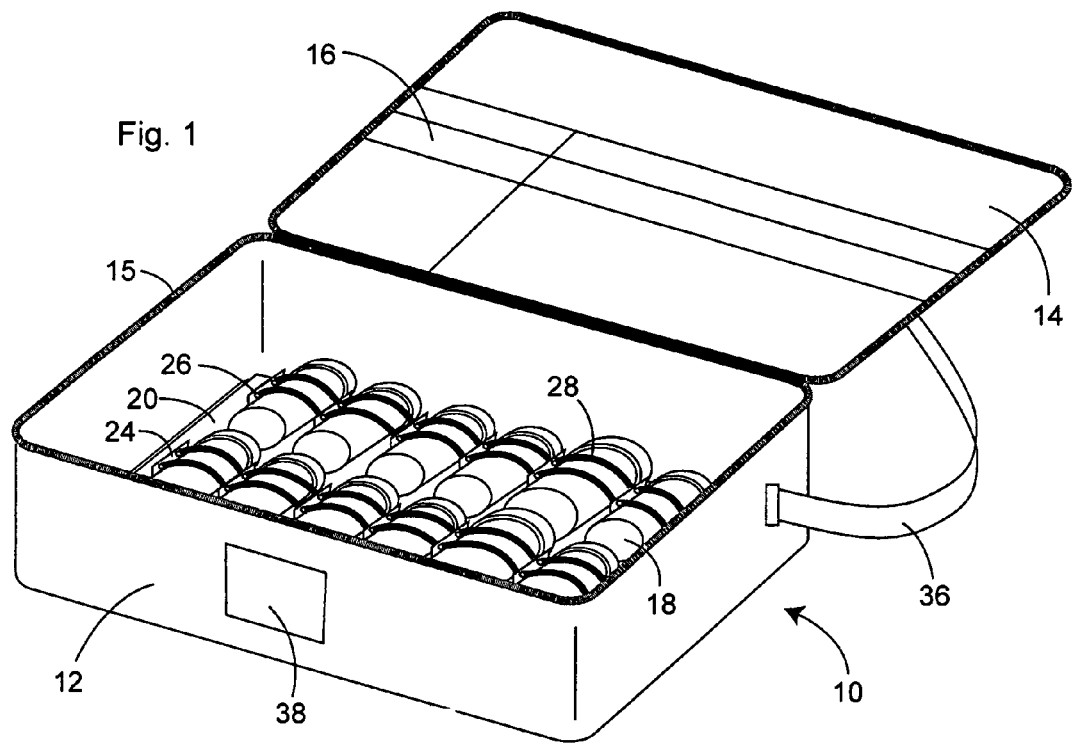
FIG. 1 is a perspective view of the medicine case of the invention.
Figure 2:
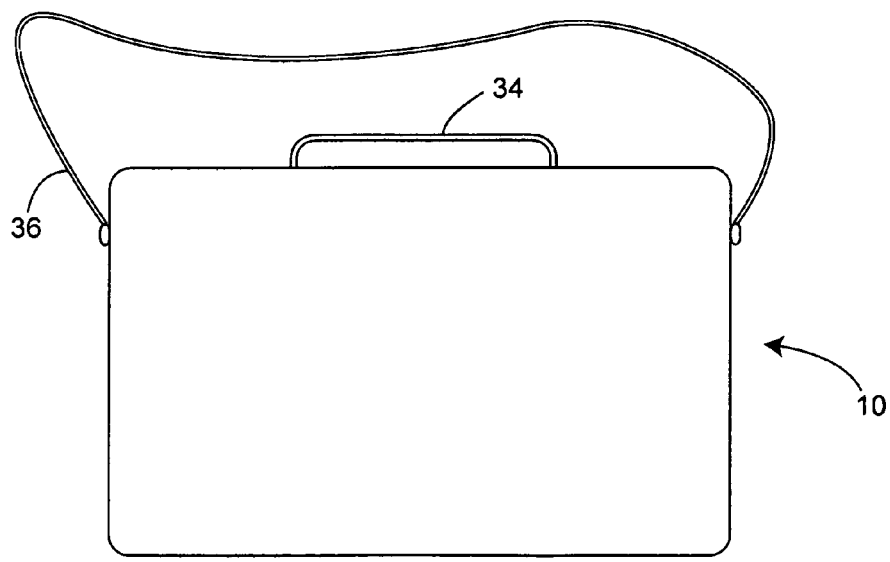
FIG. 2 is a top view of the case.

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

As illustrated in the drawings, medicine case, generally 10, is comprised of an open top box 12 with a hinged lid 14 that can be joined to the upper edge of box 12 by zipper 15. Lid 14 included a plurality of storage pockets 16.

Vials 18 are secured within box 12 with a vial holder comprised of a planar platform 20 that is releasably attached to the bottom of box 12 with hook and loop fastener 22. A plurality of spaced, parallel, flexible dividers 24 extend upwardly from the upper surface of platform 20. Each divider 24 includes a pair of left and right grommets 26 adjacent its upper edge.

An elastic cord 28 is threaded through the left grommets 26 and looped back through the right grommets 26 to form a pair of parallel cord segments. The ends of cord 28 are inserted through slidable cord lock 30 and are joined at their tips by cord pull 32.

Case 10, as illustrated in the preferred embodiment, also includes a handle 34, an adjustable and detachable shoulder strap 36, and an identification label pocket 38.

In use, vials 18 are inserted beneath the parallel segments of cord 28. Cord 28 is then tightened by pulling cord 28 through cord lock 30 so that cord 28 is snugly against vials 18. Cord 28 slides though grommets 26 to compensate for any differences in the sizes of vials 18 so that equal pressure is applied to all vials, thereby ensuring secure storage of vials of different sizes within the compartments formed by the upper surface of platform 20, the inner faces of dividers 24, and the parallel segments of cord 28.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A portable carrying case for holding a plurality of medicine vials comprising:
   a) an open-topped box having a bottom wall, spaced parallel side walls and spaced parallel end walls, the side and end walls extending upwardly from the outer periphery of the bottom wall to a common upper edge;
   b) a lid hinged to one of the side walls to extend over the top of the box;
   c) attachment means to secure the lid to the box;
   d) a vial support surface with a plurality of spaced divider walls having lower edges attached to the support surface and upper edges, each divider wall having two spaced holes adjacent the wall upper edge;
   e) a cord slidable through the divider wall holes, the support surface, walls and cord together forming a plurality of adjustable vial receiving compartments; and
   f) cord adjustment means for adjusting the length of the cord to tension the cord against vials when vials are inserted into said compartments.

2. The case of claim 1, wherein said bottom wall includes a bottom wall upper surface, said bottom wall upper surface comprising said vial support surface.

3. The case of claim 1, further including a planar platform releasably attached to said bottom wall, said platform having an upper surface comprising said vial support surface.

4. The case of claim 1, including a plurality of rows of spaced divider walls.

5. The case of claim 1, wherein said divider walls are flexible.

6. The case of claim 1, wherein grommets are inserted in each of said holes.

7. The case of claim 1, wherein said cord is elastic.

8. The case of claim 1, wherein said holes comprise aligned left holes and aligned right holes, the cord extending from a first cord end outside a first end wall through the aligned left holes to outside the opposed end wall and then through the aligned right holes to a second cord end outside said first end wall, said cord ends being joined by said cord adjustment means.

9. The case of claim 1, wherein said walls and lid are padded.

10. The case of claim 1, wherein said lid includes an inner surface with a plurality of pockets.

11. A portable carrying case for holding a plurality of medicine vials comprising:
    a) an open-topped box having a bottom wall, spaced parallel side walls and spaced parallel end walls, the side and end walls extending upwardly from the outer periphery of the bottom wall to a common upper edge;
    b) a lid hinged to one of the side walls to extend over the top of the box;
    c) attachment means to secure the lid to the box;
    d) a planar platform releasably attached to said bottom wall, said platform having an upper vial support surface with a plurality of spaced, parallel divider walls having lower edges attached to the support surface and upper edges, said divider walls having aligned left holes and aligned right holes;
    e) a looped cord slidable through the aligned left divider wall holes and then through the aligned right divider holes to cord ends outside an end divider wall, the support surface, walls and cord together forming a plurality of adjustable vial receiving compartments; and
    f) slidable cord adjustment means attached to the ends of the cord for adjusting the length of the cord to tension the cord against vials when vials are inserted into said compartments.

12. The case of claim 11, including two rows of spaced, parallel divider walls, each row including an uneven number of divider walls.

13. The case of claim 11, wherein the cord adjustment means is a spring-loaded cord lock.

14. The case of claim 11, wherein the divider walls are spaced equidistant from each other.

15. The case of claim 11, further including a carrying handle or a shoulder strap.

16. A portable carrying case for holding a plurality of medicine vials comprising:
    a) an open-topped box having a bottom wall, spaced parallel side walls and spaced parallel end walls, the side and end walls extending upwardly from the outer periphery of the bottom wall to a common upper edge;
    b) a lid hinged to one of the side walls to extend over the top of the box;
    c) a zipper to secure the lid to the box;
    d) a planar platform releasably attached to said bottom wall, said platform having an upper vial support surface with first and second parallel rows of spaced, parallel divider walls, said divider walls having lower edges attached to the support surface and upper edges, the divider walls in each row having aligned left holes and aligned right holes;
    e) each row of divider walls including a looped elastic cord slidable through the aligned left divider wall holes and then through the aligned right divider holes to cord ends outside an end divider wall, the support surface, walls and cord in each row together forming a plurality of adjustable vial receiving compartments; and f) an adjustable cord lock attached to the ends of the cord for adjusting the length of the cord to tension the cord against vials when vials are inserted into said compartments, the force on each vial being equal regardless of the vial sizes.

17. The case of claim 16, wherein said divider walls are flexible.

18. The case of claim 16, wherein the divider walls are spaced equidistant from each other.

19. The case of claim 16, said lid includes an inner surface with at least one pocket.

20. The case of claim 16, wherein said bottom wall has an upper surface and said platform has a lower surface, the platform lower surface being releasibly attached to the bottom wall upper surface with hook and loop fastener.

* * * * *